United States Patent
Zotkin et al.

(10) Patent No.: US 9,695,103 B2
(45) Date of Patent: Jul. 4, 2017

(54) ZINC OR COPPER (II) SALT AND USE THEREOF AS A BIOCIDE

(71) Applicant: LABORATORIYA BIO ZET, LLC, Moscow (RU)

(72) Inventors: Igor I. Zotkin, Nizhny Novgorod (RU); Nadezhda V. Kuznetsova, Nizhny Novgorod (RU); Larisa V. Kabanova, Nizhny Novgorod (RU)

(73) Assignee: LABORATORIYA BIO ZET, LLC, Moscow (RU)

(*) Notice: Subject to any disclaimer, the term of this patent is extended or adjusted under 35 U.S.C. 154(b) by 0 days.

(21) Appl. No.: 15/361,783

(22) Filed: Nov. 28, 2016

(65) Prior Publication Data
US 2017/0073296 A1    Mar. 16, 2017

Related U.S. Application Data

(63) Continuation of application No. PCT/RU2015/000251, filed on Apr. 20, 2015.

(30) Foreign Application Priority Data

May 27, 2014 (RU) .................... 2014121530

(51) Int. Cl.

| | | |
|---|---|---|
| C07C 51/41 | (2006.01) |
| C07C 59/50 | (2006.01) |
| A01N 55/02 | (2006.01) |
| C01G 3/00 | (2006.01) |
| C01G 9/00 | (2006.01) |
| C07C 229/24 | (2006.01) |
| C09D 5/14 | (2006.01) |
| D21H 25/02 | (2006.01) |
| C07C 229/76 | (2006.01) |
| C07F 1/00 | (2006.01) |
| C07C 55/08 | (2006.01) |
| C07C 55/10 | (2006.01) |
| C07C 57/04 | (2006.01) |
| C07C 59/06 | (2006.01) |
| C07C 59/08 | (2006.01) |
| C07C 59/105 | (2006.01) |
| C07C 59/245 | (2006.01) |
| C07C 59/255 | (2006.01) |

(52) U.S. Cl.
CPC ............. *C07C 59/50* (2013.01); *A01N 55/02* (2013.01); *C01G 3/00* (2013.01); *C01G 9/00* (2013.01); *C07C 55/08* (2013.01); *C07C 55/10* (2013.01); *C07C 57/04* (2013.01); *C07C 59/06* (2013.01); *C07C 59/08* (2013.01); *C07C 59/105* (2013.01); *C07C 59/245* (2013.01); *C07C 59/255* (2013.01); *C07C 229/24* (2013.01); *C07C 229/76* (2013.01); *C07F 1/00* (2013.01); *C09D 5/14* (2013.01); *D21H 25/02* (2013.01)

(58) Field of Classification Search
USPC ......................................... 556/114, 118, 131
See application file for complete search history.

(56) References Cited

U.S. PATENT DOCUMENTS

| | | |
|---|---|---|
| 4,258,090 A | 3/1981 | Moraru |
| 5,298,061 A | 3/1994 | Waldron et al. |
| 5,460,644 A | 10/1995 | Thomassen |
| 5,540,954 A | 7/1996 | Nicholas et al. |
| 5,717,007 A | 2/1998 | Cambon |
| 6,399,560 B1 | 6/2002 | Kwon et al. |
| 6,858,658 B2 | 2/2005 | Tomasgaard et al. |
| 7,410,553 B2 | 8/2008 | Blanpied et al. |
| 2008/0219944 A1 | 9/2008 | Longo et al. |
| 2009/0223408 A1 | 9/2009 | Richardson et al. |

FOREIGN PATENT DOCUMENTS

| | | |
|---|---|---|
| EP | 2161316 A1 | 3/2010 |
| EP | 2360214 A1 | 8/2011 |
| RU | 2315793 C1 | 1/2008 |
| RU | 2378363 C1 | 1/2010 |
| RU | 2497857 C1 * | 11/2013 |

OTHER PUBLICATIONS

International Search Report from International Application No. PCT/RU2015/000251, filed Apr. 20, 2015, mailed Jul. 9, 2015.
Chemical Abstracts Service CAS on STN comp. RN 476620-9609, publication date Dec. 18, 2002.

* cited by examiner

*Primary Examiner* — Pancham Bakshi
(74) *Attorney, Agent, or Firm* — Patentbar International, P.C.

(57) ABSTRACT

Zinc or copper (II) salt which can be used as a biocide, having the general formula $CH_2C(R^1)CO—M—OCOR^2(OH)_m(COOH)_n$ wherein M is Zn or Cu, $R^1$ is selected from the group comprising hydrogen and methyl, $R^2$ is substituted $C_1$-$C_5$ alkyl, $m=0$-$5$, $n=0$-$2$, $m+n=1$-$5$.

2 Claims, No Drawings

ZINC OR COPPER (II) SALT AND USE THEREOF AS A BIOCIDE

RELATED APPLICATIONS

This Application is a Continuation application of International Application PCT/RU2015/000251, filed on Apr. 20, 2015, which in turn claims priority to Russian Patent Applications No. RU 2014121530, tiled May 27, 2014, both of which are incorporated herein by reference in their entirety.

FIELD OF THE INVENTION

The invention relates to new chemical compounds—zinc and copper salts with organic acids, which can find application as biocides.

BACKGROUND OF THE INVENTION

Various zinc and copper compounds exhibiting biocidal activity are known in the art, in particular, zinc and copper oxides and inorganic salts (U.S. Pat. No. 5,540,954, A01N 59/16, A01N 59/20, B27K 3/52, B05D 07/06, A01N 31/08, A01N 31/00, 1996; U.S. Pat. No. 6,858,658, A01N 59/20, A01N 59/16, C09D 5/16, C08K 03/10, C08K 03/18, C08K 03/22, 2005; US 20080219944, C09D 5/16, 2008; US 20090223408, C09D 5/16, C09D 5/14, 2009), zinc and copper naphthenates or resinates (EP 2161316, C09D 133/06, C09D 133/12, C09D 143/04, C09D 5/16, C09D 7/12, 2010; EP 2360214, C09D 143/04, C09D 193/04, C09D 5/16, 2011; U.S. Pat. No. 4,258,090, C04B 41/45, C04B 41/52, C04B 41/60, C04B 41/70, B05D 03/02, 1981), ammonia complexes of zinc salts (U.S. Pat. No. 5,460,644, C08K 3/10, C08K 3/00, C09D 5/14, C09D 5/00, 1995), zinc and copper pyrithionates-bis-(2-pyridylthio)-1,1'-dioxides (U.S. Pat. No. 5,298,061, C09D 5/16, C09D 5/14, 1994; U.S. Pat. No. 5,717,007, C09D 5/16, C08L, 33/10, C08K 05/17, C08K 05/18, 1998; U.S. Pat. No. 6399560, A01N 43/40, A01N 43/34, A61L 2/18, C11D 3/48, 2002; U.S. Pat. No. 7,410,553, D21C 5/02, B32B 27/04, D21G 1/02, 2008). The above mentioned compounds were used with various degrees of efficiency as biocide of different purpose.

Zinc salt with acetic and methacrylic acids, i.e. zinc methacrylate-acetate (hereinafter referred to as ZMA) exhibiting a certain biocidal activity when compounded with aqueous styrene-acrylic dispersion being used as polymer primer for applying paint coatings to various surfaces is also known (RU 2315793, C09D 5/14, C09D 131/02, C09D 133/10, 2008).

The closest analogue of the proposed compounds is zinc or copper (II) salt of the general formula

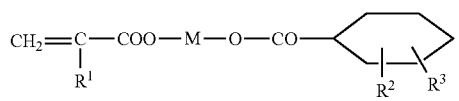

wherein M—Zn or Cu,
$R^1$ is selected from the group comprising hydrogen and methyl,
$R^2$ is selected from the group comprising hydrogen, alkyl and $SO_2OH$ group.
$R^3$ is selected from the group comprising hydrogen and OH (RU 2497857, C09D 5/14, C07C 69/78).

SUMMARY OF THE INVENTION

To provide new means effecting on various biological substrates zinc or copper (II) salt of the general formula is proposed:

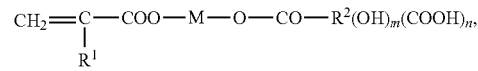

wherein M—Zn or Cu,
$R^1$ is selected from the group comprising hydrogen and methyl,
$R^2$ is substituted $C_1$-$C_5$ alkyl,
m=0-5
n=0-2
m+n=1-5

To solve the same problem it is also proposed to use the above compound as biocide.

It was found that zinc and copper (II) salts corresponding to the above formula exhibit high biocidal activity and wide spectrum of effect on biological matters. Thus, they can be used in disinfectant compositions of various purposes, coating compositions, paper and wood treatment compositions, polymer compositions with higher fungus resistance as well as in many processes preventing organisms and materials from adverse effect of biological matters, in particular crustaceans.

DETAILED DESCRIPTION OF THE PREFERRED EMBODIMENTS

The essence of the invention is illustrated by examples given below. Examples 1-11 describe the preparation and properties of certain representatives of the proposed series of substances, examples 12-28 various types of their biocidal activity,

EXAMPLE 1

10 g of glycolic acid, 100 ml of distilled water are placed into a 500 ml round-bottom flask, and the solution is stirred until glycolic acid is completely dissolved. Then a suspension of 10.6 g of copper (II) oxide in 50 ml of distilled water is gradually added to the solution under constant stirring, whereupon 11.32 g of methacrylic acid is added, and the suspension is stirred until completely dissolving solids. The obtained solution is evaporated to dryness at a temperature of not more than 70° C., and the resulted solid product is subjected to recrystallization from distilled water, 28 g of water-soluble powdered copper methacrylate-glycolate is obtained which corresponds to the above general formula wherein $R^1$=$CH_3$, $R^2$=$CH_2$, m=1, n=0 (95% yield of the stoichiometric), The results of elemental analysis of salts obtained as described in this and subsequent examples are given in Table 1.

EXAMPLE 2

Copper methacrylate-alutamate ($R^1$=$CH_3$, $R^2$=CH($NH_2$)($CH_2$)$_2$, m=0, n=1) with melting point of 200° C. is obtained in 75% yield of the stoichiometric by analogy with Example 1 using glutamic acid instead of glycolic one.

EXAMPLE 3

Copper acrylate-asparaginate ($R^1$=H, $R^2$=CH($NH_2$)$CH_2$, m=0, n=1) with melting point of 185° C. is obtained in 82% yield of the stoichiometric by analogy with Example 1 using acrylic and asparaginic acids instead of methacrylic and glycolic ones (respectively).

EXAMPLE 4

Zinc methacrylate-succinate ($R^1$=$CH_3$, $R^2$=$(CH_2)_2$, m=0, n=1) with melting point of 195° C. is obtained in 74% yield of the stoichiometric by analogy with Example 1 using succinic acid instead of alycolic one and zinc oxide instead of copper one.

EXAMPLE 5

Zinc acrylate-malonate ($R^1$=H, $R^2$=$CH_2$, m=0, n=1) with melting point of 175° C. is obtained in 78% yield of the stoichiometric by analogy with Example 1 using acrylic and malonic acids instead of methacrylic and glycolic ones (respectively) and zinc oxide instead of copper one.

EXAMPLE 6

Zinc methacrylate-malate ($R^1$=$CH_3$, $R^2$=$CH_2CH$, m=1, n=1) with melting point of 215° C. is obtained in 78% yield of the stoichiometric by analogy with Example 1 using malic acid instead of glycolic one and zinc oxide instead of copper one.

EXAMPLE 7

Zinc acrylate-citrate($R^1$=H, $R^2$=$C(CH_2)_2$, m=1, n=2) with melting point of 155° C. is obtained in 87% yield of the stoichiometric by analogy with Example 1 using acrylic and citric acids instead of methacrylic and glycolic ones (respectively) and zinc oxide instead of copper one.

EXAMPLE 8

Zinc acrylate-amygdalate ($R^1$=$R^2$=$CHC_6H_5$, m=1, n=0) with melting point of 180° C. is obtained in 65% yield of the stoichiometric by analogy with Example 1 using acrylic and amygdalic acids instead of methacrylic and glycolic ones (respectively) and zinc oxide instead of copper one.

EXAMPLE 9

Copper acrylate-tartrate ($R^1$=H, $R^2$=CHCH, m=2, n=1) with melting point of 165° C. is obtained in 78% yield of the stoichiometric by analogy with Example 1 using acrylic and tartaric acids instead of methacrylic and glycolic ones (respectively).

EXAMPLE 10

Zinc acrylate-lactate ($R^1$=H, $R^2$=$CHCH_3$, m=1, n=0) with melting point of 175° C. is obtained in 65% yield of the stoichiometric by analogy with Example 1 using acrylic and lactic acids instead of methacrylic and glycolic ones (respectively) and zinc oxide instead of copper one.

EXAMPLE 11

Copper acrylate-gluconate ($R^1$=H, $R^2$=$(CH)_4CH_2$, m=5, n=0) with melting point of 195° C. is obtained in 68% yield of the stoichiometric by analogy with Example 1 using acrylic and &conic acids instead of methacrylic and glycolic ones (respectively).

EXAMPLE 12

Bactericidal activity of copper methacrylate-glycolate obtained as described in Example 1, copper acrylate-tartrate obtained as described in Example 9 and zinc acrylate-malonate obtained as described in Example 5 is determined according to the known method (RU 2378363, C12N 1/00, C12Q 1/00, 2010) based on the exposure of a bacterial culture in a solution of bactericidal substance for a certain period of time followed by its neutralization and inoculation of the culture on a solid nutrient medium. The sensitivity of microorganisms to a disinfectant is judged by microorganism growth on the nutrient medium up to 300 CFU/ml (CFU colony-forming unit) while growth up to 100 CFU/ml indicates incomplete bactericidal effect, growth up to 100-300 CFU/ml indicates sub-bactericidal effect and growth up to more than 300 CFU/ml indicates resistance of microorganisms to a disinfectant, The determination is performed on *E. coli* No. 906 and *S. aureus* No. 1257 test strains conventionally used to study the bactericidal activity of biocides as well as on clinical strain *P. aeruginosa* at salt concentrations from 1.5 to 3% and time of exposure from 5 to 60 min. Test results are given in Table 2. It follows from Table 2 that copper methacrylate-glycolate, copper acrylate-tartrate and zinc acrylate-malonate at concentration of 2.0% exhibit stable bactericidal effect against investigated strains at time of exposure from 30 min.

EXAMPLES 13-24

The fungicidal activity of the proposed salts is determined according to GOST 30028.4-2006 by testing samples of various materials treated with these salts for resistance to fungal spores, Test results in terms of tolerance time (in days) are given in Table 3 wherein tolerance time for untreated materials are given for comparison,

EXAMPLES 25-26

The biocidal activity of copper methacrylate-glycolate obtained as described in Example 1 and zinc acrylate-lactate obtained as described in Example 10 against crustaceans (daphnias) is tested according to FR. 1.39.2007,03223 procedure, Test results for salts obtained as described in these and subsequent examples are given in Table 4.

Examples 27-28 (comparative). The biocidal activity of known compounds is tested in conditions described in Examples 25-26,

INDUSTRIAL APPLICABILITY

The present invention can be used for production of biocides intended, for example, for incorporation into polymer compositions, disinfectant and antiseptic compositions, treatment of wood, paper, building structures and other materials to prevent their damage caused by biological matters (microorganisms, fungi, algae), manufacture of various articles with biocidal properties, etc.

TABLE 1

Results of elemental analysis of salts

| Example 1 | Name 2 | Empirical formula 3 | Sample weight, g 4 | C, g calculated 5 | C, g determined 6 | H, g calculated 7 | H, g determined 8 |
|---|---|---|---|---|---|---|---|
| 1 | Copper methacrylate-glycolate | $C_6H_8O_5Cu$ | 0.5 | 0.1609 | 0.161<br>0.1609 | 0 0180 | 0.0179 |
| 2 | Copper methacrylate-glutamate | $C_9H_{13}O_6NCu$ | 0.5 | 0.183 | 0.18<br>0.184 | 0.022 | 0.021<br>0.02 |
| 3 | Copper acrylate-asparginate | $C_7H_9O_6NCu$ | 0.5 | 0.1575 | 0.157<br>0.151 | 0.0168 | 0.016<br>0.017 |
| 4 | Zinc methacrylate-succinate | $C_8H_{10}O_6Zn$ | 0.5 | 0.1795 | 0.18<br>0.178 | 0.0187 | 0.019<br>0.0185 |
| 5 | Zinc acrylate-malonate | $C_6H_6O_6Zn$ | 0.5 | 0.15 | 0.148<br>0.151 | 0.0125 | 0.013<br>0.0125 |
| 6 | Zinc methacrylate-malate | $C_8H_{10}O_7Zn$ | 0.5 | 0.1695 | 0.169<br>0.17 | 0.0176 | 0.0179<br>0.0177 |
| 7 | Zinc acrylate-citrate | $C_9H_{10}O_9Zn$ | 0.5 | 0.165 | 0.164<br>0.167 | 0.0153 | 0.0153<br>0.0151 |
| 8 | Zinc acrylate-amygdalate | $C_{11}H_{10}O_5Zn$ | 0.5 | 0.2295 | 0.23<br>0.229 | 0.0174 | 0.0175 |
| 9 | Copper acrylate-tartrate | $C_7H_8O_8Cu$ | 0.5 | 0.148 | 0.15<br>0.149 | 0.014 | 0.014<br>0.0145 |
| 10 | Zinc acrylate-lactate | $C_6H_8O_5Zn$ | 0.5 | 0.159 | 0.16 | 0.0177 | 0.018 |
| 11 | Copper acrylate-gluconate | $C_9H_{14}O_9Cu$ | 0.5 | 0.1638 | 0.164<br>0.165 | 0.0212 | 0.021 |

| Example 1 | Zn, g calculated 9 | Zn, g determined 10 | Cu, g calculated 11 | Cu, g determined 12 | N, g calculated 13 | N, g determined 14 |
|---|---|---|---|---|---|---|
| 1 | | | 0.1421 | 0.1420<br>0.1421 | | |
| 2 | | | 0.108 | 0.11 | 0.0237 | 0.024 |
| 3 | | | 0.1193 | 0.119 | 0.0262 | 0.027 |
| 4 | 0.122 | 0.12<br>0.116 | | | | |
| 5 | 0.137 | 0.14 | | | | |
| 6 | 0.115 | 0.115<br>0.117 | | | | |
| 7 | 0.0998 | 0.1<br>0.099 | | | | |
| 8 | 0.1137 | 0.1138 | | | | |
| 9 | | | 0.112 | 0.1125 | | |
| 10 | 0.145 | 0.147 | | | | |
| 11 | | | 0.0964 | 0.0968<br>0.0962 | | |

TABLE 2

Bactericidal activity of salts

| Concentration, % wt. | Time of exposure, min. | Copper methacrylate-glycolate E. coli 906 | Copper methacrylate-glycolate S. aureus 1257 | Copper methacrylate-glycolate P. aeruginosa | Copper acrylate-tartrate E. coli 906 | Copper acrylate-tartrate S. aureus 1257 | Copper acrylate-tartrate P. aeruginosa | Zinc acrylate-malonate E. coli 906 | Zinc acrylate-malonate S. aureus 1257 |
|---|---|---|---|---|---|---|---|---|---|
| 3.0 | 30 | NG | NG | NG | NG | NG | NG | | |
| | 15 | NG | NG | NG | NG | NG | NG | | |
| | 5 | NG | NG | NG | NG | NG | NG | | |
| 2.0 | 60 | NG | NG | NG | NG | NG | NG | NG | NG |
| | | NG | NG | NG | NG | NG | NG | NG | NG |
| | | NG | NG | NG | NG | NG | NG | NG | NG |
| | | NG | NG | NG | NG | NG | NG | NG | NG |
| | 30 | NG | NG | NG | NG | NG | NG | NG | NG |
| | | NG | NG | >300 CFU | NG | NG | NG | NG | NG |

TABLE 2-continued

Bactericidal activity of salts

| Concentration, % wt. | Time of exposure, min. | Copper methacrylate-glycolate | | | Copper acrylate-tartrate | | | Zinc acrylate-malonate | |
|---|---|---|---|---|---|---|---|---|---|
| | | E. coli 906 | S. aureus 1257 | P. aeruginosa | E. coli 906 | S. aureus 1257 | P. aeruginosa | E. coli 906 | S. aureus 1257 |
| | | NG | NG | >300 CFU | NG | NG | >300 CFU | NG | NG |
| | | | | | | | | | NG |
| | 15 | >300 CFU | >300 CFU | >300 CFU | NG | NG | >300 CFU | NG | NG |
| | 5 | CG | CG | CG | NG | NG | CG | 1 CFU | NG |
| 1.5 | 60 | >300 CFU | >300 CFU | CG | NG | NG | CG | 5 CFU | 1 CFU |
| | | | | | NG | NG | | 4 CFU | 3 CFU |
| | | | | | NG | NG | | | |
| | 30 | CG | CG | CG | | | CG | 45 CFU | 35 CFU |
| | | | | | | | | 53 CFU | 43 CFU |
| | 15 | | | | | | — | 78 CFU | 85 CFU |
| | 5 | | | | | | — | >300 CFU | >300 CFU |

Note:
NG - no growth;
CFU - number of colony-forming units in 1 ml;
CG - confluent growth

TABLE 3

Fungicidal activity of salts

| Example No. | Test material | Additive Name | Content, % wt. | Tolerance time, days |
|---|---|---|---|---|
| 13 | Polyvinyl chloride emulsion | Copper methacrylate-glycolate | 5 | 10 |
| 14 | Polyvinyl chloride emulsion | Copper acrylate-tartrate | 5 | 17 |
| 15 | Polyvinyl chloride emulsion | Zinc methacrylate-malate | 5 | 9 |
| 16 | Polyvinyl chloride emulsion | Zinc acrylate-citrate | 5 | 17 |
| 17 | Polyvinyl chloride emulsion | Zinc acrylate-malonate | 5 | 18 |
| 18 (compar.) | Polyvinyl chloride emulsion | — | — | 6 |
| 19 | Paper impregnated with latex SKS 65 GP | Copper methacrylate-glycolate | 5 | 8 |
| 20 | Paper impregnated with latex SKS 65 GP | Copper acrylate-tartrate | 5 | 16 |
| 21 | Paper impregnated with latex SKS 65 GP | Zinc acrylate-malonate | 5 | 20 |
| 22 (compar.) | Paper impregnated with latex SKS 65 GP | — | — | 4 |
| 23 | Paper impregnated with petrolatum base | Copper methacrylate-glycolate | 5 | 8 |
| 24 (compar.) | Paper impregnated with petrolatum base | — | — | 5 |

Table 4

Biocidal activity of compounds against crustaceans

| Example No. | Compound | Concentration in aqueous medium, % wt. | Test time, h | Number of survived daphnias (the average over parallel set of samples) Control sample | Test sample | Daphnia death rate in test sample, % of control sample |
|---|---|---|---|---|---|---|
| 25 | Zinc acrylate-lactate | 1 | 96 | 10 | 0 | 100 |
| | | 0.1 | | | 0 | 100 |
| | | 0.01 | | | 0 | 100 |
| | | 0.001 | | | 0 | 100 |
| | | 0.0001 | | | 1 | 90 |
| | | 0.001 | | | 3 | 70 |
| 26 | Copper methacrylate-glycolate | 1 | 96 | 10 | 0 | 100 |
| | | 0.1 | | | 0 | 100 |
| | | 0.01 | | | 0 | 100 |
| | | 0.001 | | | 0 | 100 |
| | | 0.0001 | | | 0 | 100 |
| | | 0.00001 | | | 1 | 90 |
| 27 (compar.) | Copper acrylate-benzoate | 1 | 96 | 10 | 8 | 20 |
| | | 0.1 | | | 9 | 10 |
| | | 0.01 | | | 10 | 0 |
| | | 0.001 | | | 10 | 0 |
| | | 0.0001 | | | 10 | 0 |
| | | 0.00001 | | | 10 | 0 |
| 28 (compar.) | Zinc methacrylate-salicylate | 1 | 96 | 10 | 10 | 0 |
| | | 0.1 | | | 10 | 0 |
| | | 0.01 | | | 10 | 0 |
| | | 0.001 | | | 10 | 0 |
| | | 0.0001 | | | 10 | 0 |
| | | 0.00001 | | | 10 | 0 |

What is claimed is:
1. A zinc or copper (II) salt having a general formula
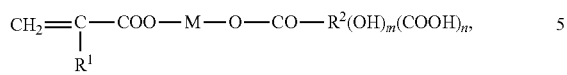
wherein M is Zn or Cu,
R$^1$ is selected from the group consisting of hydrogen and methyl
R$^2$ is substituted C$_1$-C$_5$ alkyl,
m=0-5
n=0-2
m+n=1-5.
2. The salt according to claim 1, wherein the zinc or copper salt is used as a biocide.
* * * * *